United States Patent
Berghofer et al.

(10) Patent No.: US 10,662,150 B2
(45) Date of Patent: May 26, 2020

(54) SULFONIC ACID SALT COMPOSITION AND USE THEREOF FOR COLOR STABILIZATION

(71) Applicant: L. BRÜGGEMANN GMBH & CO. KG, Heilbronn (DE)

(72) Inventors: Josef Berghofer, Tauberbischofsheim (DE); Stefan Mark, Bad Rappenau (DE); Tamara Bittlingmayer, Weinsberg (DE); Jessica Schreiweis, Obrigheim (DE)

(73) Assignee: L. BRÜGGEMANN GMBH & CO. KG, Heilbronn (DE)

( * ) Notice: Subject to any disclaimer, the term of this patent is extended or adjusted under 35 U.S.C. 154(b) by 0 days.

(21) Appl. No.: 16/467,377

(22) PCT Filed: Dec. 12, 2017

(86) PCT No.: PCT/EP2017/082449
§ 371 (c)(1),
(2) Date: Jun. 6, 2019

(87) PCT Pub. No.: WO2018/108925
PCT Pub. Date: Jun. 21, 2018

(65) Prior Publication Data
US 2020/0095198 A1    Mar. 26, 2020

(30) Foreign Application Priority Data
Dec. 13, 2016 (EP) ..................................... 16203719

(51) Int. Cl.
*C07C 309/17* (2006.01)
*C08F 220/06* (2006.01)

(52) U.S. Cl.
CPC .......... *C07C 309/17* (2013.01); *C08F 220/06* (2013.01)

(58) Field of Classification Search
None
See application file for complete search history.

(56) References Cited

U.S. PATENT DOCUMENTS

| 6,586,622 B2 * | 7/2003 | Berghofer ............ D21C 9/1084 562/126 |
| 2002/0042353 A1 | 4/2002 | Berghofer et al. |
| 2013/0256593 A1 | 10/2013 | Herfert et al. |

FOREIGN PATENT DOCUMENTS

| DE | 10 2007 053 619 A1 | 5/2009 | |
| EP | 1 201 685 A2 | 5/2002 | |
| WO | WO 99/18067 A1 | 4/1999 | |
| WO | WO-9918067 A1 * | 4/1999 | .............. D06P 5/155 |
| WO | WO 2004/084962 A1 | 10/2004 | |
| WO | WO 2013/021234 A1 | 2/2013 | |
| WO | WO 2013/160711 A1 | 10/2013 | |

OTHER PUBLICATIONS

International Search Report, issued in PCT/EP2017/082449, dated Mar. 8, 2018.
Written Opinion of the International Searching Authority, issued in PCT/EP2017/082449, dated Mar. 8, 2018.

* cited by examiner

*Primary Examiner* — Yong L Chu
(74) *Attorney, Agent, or Firm* — Birch, Stewart, Kolasch & Birch, LLP

(57) ABSTRACT

A sulfonic acid salt composition includes compounds of formula (I), wherein n is 1 or 2, $R^1$ is H or $C_1$-$C_6$ alkyl, $R^2$ is COOM, $SO_3M$ or $CH(OH)SO_2$—OM, each M is an equivalent of a multivalent metal, preferably magnesium, calcium, aluminum, zinc and combinations thereof. The molar ratio of a compound wherein n is 1 to a compound wherein n is 2 is below 0.1. The sulfonic acid salt composition is useful for color stabilization of non-living organic matter such as from lacquers, paints, powder-coatings, and polymers in particular water-absorbent polymers.

20 Claims, No Drawings

SULFONIC ACID SALT COMPOSITION AND USE THEREOF FOR COLOR STABILIZATION

The invention relates to a sulfonic acid salt composition and its use for color stabilization of non-living organic matter.

BACKGROUND

It is known that non-living organic matter such as lacquers, paints, powder-coatings, and polymers can undergo a color change, such as yellowing, on aging.

An important example of polymers that are prone to color change are superabsorbent polymers. Superabsorbent polymers (SAPs) are well known in the art. They are commonly used in sanitary and hygienic articles, such as diapers, training pants, adult incontinence products and feminine care products to increase the absorbent capacity of such products while reducing their overall bulk. SAPs are capable of absorbing and retaining amounts of aqueous fluids equivalent to many times their own weight, even under moderate pressure. Typically, SAPs are lightly crosslinked hydrophilic polymers, like partially neutralized, crosslinked polyacrylic acid.

SAPs have a tendency to degrade in color after long periods of storage. The tendency of an SAP to undergo a color transition from a bright white color to a honey brown color accelerates as storage time, temperature, and humidity increase. In temperate climates, such as the United States and Europe, the rate at which an SAP undergoes color degradation is sufficiently slow such that the SAP, or article containing the SAP, typically is consumed before a color change is observable to the naked eye.

However, in tropical and subtropical climates, such as in South America and Southeast Asia, SAP color degradation is sufficiently rapid such that a color change often occurs before the SAP, or article containing the SAP, is consumed. This problem is exacerbated when the SAPs is produced far from the tropical climate, thereby increasing the time span from SAP production to use.

Even though the change in color of the SAP does not affect SAP performance, it adversely affects consumer acceptance of articles containing the color-degraded SAPs. In particular, consumers observing a color-degraded SAP in a diaper form an opinion that the diaper contains a contaminant, is somehow soiled or faulty, or is of low quality.

It has been suggested to use sulfurous reducing agents to stabilize nonliving organic matter such as SAPs against color change and impart color stability properties to the nonliving organic matter.

WO 2004/084962 relates to a method of manufacturing color-stable superabsorbent polymer particles which involves the use of a monomer mixture containing a polymerization initiator comprising a sulfinic acid derivative, such as 2-hydroxy-2-sulfinatoacetic acid, or a salt thereof.

DE 10 2007 053 619 relates to a method for the production of water-absorbing polymer structures, wherein a reducing agent containing a sulfonate, a salt of a sulfonate, or a mixture of a sulfonate and a salt of a sulfonate is added during the production method.

US 2013/0256593 discloses a superabsorbent obtainable by polymerizing a monomer solution, drying the resulting polymer and optionally surface-crosslinking the dried polymer, wherein a sulfonic acid derivative is added to the monomer mixture or to the polymer prior to drying. The preferred sulfonic acid derivative is 2-hydroxy-2-sulfonatoacetic acid disodium salt.

WO 99/18067 discloses sulfinic acid derivatives which can be used as reducing agents which do not release formaldehyde. Specifically, WO 99/18067 discloses a zinc salt composition of 2-hydroxy-2-sulfinatoacetic acid and 2-hydroxy-2-sulfonatoacetic acid comprising 20 wt.-% of sulfinic acid and 48 wt.-% of sulfonic acid.

Whereas sulfinic acid derivatives such as 2-hydroxy-2-sulfinatoacetic acid salts have strong reducing power they are less satisfactory in long term color stabilization. Sulfonic acid derivatives such as 2-hydroxy-2-sulfonatoacetic acid salts, albeit being weaker reducing agents, are more desirable for color stabilization.

For ease of dosage the sulfurous reducing agents are preferably added to the monomer mixture or the superabsorbent polymer as a solution, in particular as an aqueous solution. Especially if the solution is applied to the dried polymer or finished superabsorbent polymer it is desirable to use highly concentrated solutions in order to minimize water input or to avoid the necessity of a subsequent drying step. Unfortunately, the commercially available 2-hydroxy-2-sulfonatoacetic acid disodium salt exhibits poor aqueous solubility. There is a need for 2-hydroxy-2-sulfonatoacetic acid derivatives having higher aqueous solubility.

In addition, the known sulfurous reducing agents result in a characteristic unpleasant odor of the treated matter. Some of the reducing agents are inherently malodorous or produce side reactions products that are malodorous. Such unpleasant odor is particularly undesirable in sanitary and hygienic articles. The unpleasant odor of sulfurous reducing agents is also undesirable for reasons of occupational safety and health protection during the production of the superabsorbent polymers or the sanitary and hygienic articles manufactured therefrom.

SUMMARY OF THE INVENTION

The present invention seeks to provide reducing agents suitable for color stabilization, having increased aqueous solubility. Further, the invention is directed to overcoming the odor problems associated with sulfurous reducing agents used for color stabilization while maintaining color stabilization properties.

This problem is solved by a sulfonic acid salt composition comprising compounds of formula (I)

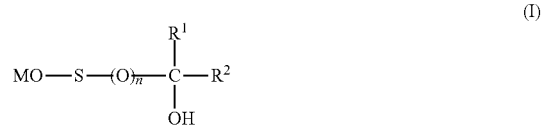

wherein
n is 1 or 2,
$R^1$ is H or $C_1$-$C_6$ alkyl,
$R^2$ is COOM, $SO_3M$ or $CH(OH)SO_n$-OM,
each M is an equivalent of a multivalent metal, and
the molar ratio of a compound wherein n is 1 to a compound wherein n is 2 is below 0.1.

DETAILED DESCRIPTION OF THE INVENTION

The term "$C_1$-$C_6$ alkyl" as used herein means a straight or branched alkyl group having 1 to 6 carbon atoms. Examples are methyl, ethyl, n-propyl, isopropyl, n-butyl, sec-butyl, isobutyl, tert-butyl, n-pentyl and n-hexyl.

$R^1$ is preferably H. $R^2$ is preferably —COOM. Further preferred are compounds of formula (I) wherein $R^1$ is H and $R^2$ is —COOM.

In formula (I), each M is an equivalent of a multivalent metal. An "equivalent" is the fictitious fraction of the multivalent metal corresponding to a single valence. M can comprise one kind of a multivalent metal or a combination of multivalent metals. M does not comprise monovalent metals such as alkali metals. In particular the multivalent metal(s) are bivalent and/or trivalent metals. Preferably, M is selected from groups 2, 4, 12 and 13 of the Periodic Table of Elements (IUPAC numbering).

In preferred embodiments, M is selected from magnesium, calcium, aluminum, zinc and combinations thereof.

In other preferred embodiments, M comprises a combination of first metal $M^1$ and a second metal $M^2$, wherein $M^1$ is selected from zinc, calcium and aluminum, and $M^2$ is magnesium. Preferably, M comprises, on an equivalent basis, 10 to 70 mole % of $M^1$ and 30 to 90 mole % of $M^2$, preferably 10 to 45 mole % of $M^1$ and 55 to 90 mole % of $M^2$.

The molar ratio of a compound wherein n is 1 to a compound wherein n is 2 is below 0.1. Preferably, the sulfonic acid salt composition is essentially free of a compound of formula (I) wherein n is 1.

In an embodiment, the invention relates to a sulfonic acid salt of formula (Ia)

(Ia)

wherein $R^1$, $R^2$ and M are defined as above. Preferably, the sulfonic acid salt of formula (Ia) contains 10 wt.-% or less, or 5 wt.-% or less, of sulfur compounds other than compounds of formula (Ia), based on the total weight of the sulfonic acid salt of formula (Ia).

In an embodiment, the invention relates to a magnesium salt of a compound of formula (Ib)

(Ib)

wherein $R^1$ is H or $C_1$-$C_6$ alkyl, preferably H.

In a further embodiment, the invention relates to a zinc salt of a compound of formula (Ib).

In a further embodiment, the invention relates to a mixed magnesium-zinc salt of a compound of formula (Ib). Preferably, the cation of the mixed magnesium-zinc salt comprises, on an equivalent basis, 10 to 70 mole % of zinc and 30 to 90 mole % of magnesium, preferably 10 to 45 mole % of zinc and 55 to 90 mole % of magnesium, particularly preferred 20 to 45 mole % of zinc and 55 to 80 mole % of magnesium.

In a further embodiment, the invention relates to a mixed aluminum-magnesium salt of a compound of formula (Ib). Preferably, the cation of the mixed aluminum-magnesium salt M comprises, on an equivalent basis, 10 to 70 mole % of aluminum and 30 to 90 mole % of magnesium, preferably 10 to 45 mole % of aluminum and 55 to 90 mole % of magnesium.

In a further embodiment, the invention relates to a mixed calcium-magnesium salt of a compound of formula (Ib). Preferably, the cation of the mixed calcium-magnesium salt comprises, on an equivalent basis, 10 to 70 mole % of calcium and 30 to 90 mole % of magnesium, preferably 10 to 45 mole % of calcium and 55 to 90 mole % of magnesium.

A further aspect of the invention is a process for preparing the compositions of the invention.

Sulfonic acid salt compositions according to the invention are obtainable by reacting a compound of formula (II)

(II)

with a metal bisulfite

wherein
$R^1$ is H or $C_1$-$C_6$ alkyl,
$R^{2a}$ is $COOM^1$, $SO_3M^1$ or CHO,
$M^1$ and $M^2$ each are an equivalent of a multivalent metal which can be identical or different.

In particular, $M^1$ and $M^2$ are independently selected from magnesium, calcium, aluminum, and zinc. In preferred embodiments $M^1$ is selected from zinc, calcium and aluminum, and $M^2$ is magnesium. Preferably, the pH of the reaction medium is adjusted to 4 to 5 by addition of an oxide or hydroxide of $M^1$.

The above process results in sulfonic acid salt compositions comprising compounds of formula (I) wherein n is 2 which are free of compounds of formula (I) wherein n is 1.

Specifically, compositions wherein $R^2$ is COOM are obtainable by reacting a glyoxylic acid salt of a first metal $M^1$ with a bisulfite salt of a second metal $M^2$, wherein $M^1$ and $M^2$ each are multivalent metals which can be identical or different. In particular, $M^1$ and $M^2$ are independently selected from magnesium, calcium, aluminum, and zinc. In preferred embodiments $M^1$ is selected from zinc, calcium and aluminum, and $M^2$ is magnesium. In an especially preferred embodiment, $M^1$ is zinc and $M^2$ is magnesium. Generally, the reaction is carried out in an aqueous medium. Preferably, the pH of the reaction medium is adjusted to 4 to 5 by addition of an oxide or hydroxide of $M^1$.

Conveniently, the glyoxylic acid salt of the first metal $M^1$ can be prepared by reacting glyoxylic acid with an oxide or hydroxide of $M^1$ in an aqueous medium. The glyoxylic acid salt of the first metal $M^1$ can be reacted in a one-pot reaction with the bisulfite salt of the second metal $M^2$ without prior isolation or purification.

Analogously, compositions wherein $R^2$ is $SO_3M$ are obtainable by reacting a 1-oxo-methanesulfonic acid salt of a first metal $M^1$ with a bisulfite salt of a second metal $M^2$, wherein $M^1$ and $M^2$ have the meanings given above.

Compositions wherein $R^2$ is $CH(OH)SO_2$—OM are obtainable by reacting glyoxal with a bisulfite salt of a metal M, wherein M is a metal selected from magnesium, calcium, aluminum, zinc and combinations thereof. In preferred embodiments M comprises a combination of first metal $M^1$ and a second metal $M^2$, wherein $M^1$ and $M^2$ have the meanings given above.

The compositions of the invention can be recovered by drying of the reaction mixture without prior purification. Drying can be accomplished in a conventional manner, for example by spray drying. Alternatively, the compositions of the invention can be recovered by crystallization or precipitation. For this purpose a water-miscible solvent may be added to the reaction mixture obtained to precipitate the salts. Suitable solvents include methanol, ethanol, propanol, isopropanol, acetone, methyl ethyl ketone and the like. The salts can then be separated and dried in a conventional manner.

The salts of the invention may be provided in solid form, for example as a powder or granulate, or as an aqueous solution or suspension. The solid salts and an aqueous solution thereof are storage stable for a long period of time. Even after storage of the solution for 21 days at a pH of 5 the reducing power of the solution is only very slightly reduced. The water content of the salts of the invention in solid form is, in general, in the range of 0.1 to 4 wt. %, based on dry solids.

For use the salts may be applied in solid form, as an aqueous solution or an aqueous suspension which may be freshly prepared. For example, the aqueous solution or suspension may comprise 10 to 50 wt. % of the compound or composition, based on the total weight of the solution or suspension.

The inventive sulfonic acid salt compositions are suitable for color stabilization of non-living organic matter, in particular against oxidation-induced discolorization. The organic matter often contains traces of latently chromogenic contaminants. Oxidation of these latently chromogenic contaminants results in colored products which cause discolorization of the organic matter. Alternatively, oxidative degradation of organic matter can result in colored products. The inventive sulfonic acid salt compositions can prevent or reduce the discolorization caused by these mechanisms.

The non-living organic matter can be selected from lacquers, paints, powder-coatings, and polymers. In preferred embodiments, the polymer is selected from water-absorbent polymers.

Typically, water-absorbent polymers are prepared by a process comprising the steps of:
(i) providing an aqueous monomer solution containing a polymerizable, monoethylenically unsaturated monomer (M1) carrying acid groups or a salt thereof, a crosslinking agent, and optionally a monoethylenically unsaturated monomer (M2) which can be copolymerized with the monomer (M1),
(ii) radically polymerizing the aqueous monomer solution to obtain a polymer gel,
(iii) optionally, comminutating the polymer gel,
(iv) drying the polymer gel to obtain a dried water-absorbent polymer,
(v) optionally grinding and sieving the dried water-absorbent polymer to obtain a particulate water-absorbent polymer, and
(vi) surface crosslinking particulate water-absorbent polymer.

Mostly, the monoethylenically unsaturated monomer (M1) is acrylic acid or methacrylic acid, preferably acrylic acid, which can be partially neutralized.

The inventive sulfonic acid salt compositions can be added to the monomer solution and/or polymer gel and/or the water-absorbent polymer at any step of the manufacturing process. The inventive sulfonic acid salt compositions can be incorporated In the aqueous monomer solution of step (i) or be added to the polymer gel obtained in step (ii). Generally, however, it is preferred to add inventive sulfonic acid salt compositions to the particulate water-absorbent polymer after step (v) or (vi).

The examples below illustrate the invention without limiting it.

EXAMPLE 1

Synthesis of a Zinc-Salt of 2-Hydroxy-2-Sulfonatoacetic Acid

Under ice-cooling, 29.6 g of glyoxylic acid (50% aqueous solution) was solved in 100 g of demineralized water and treated with 8.1 g of zinc oxide in portions. 36.2 g of zinc sulphite dehydrate was added to the reactor and afterwards stirred for 1 h at room temperature. Then, the pH value was adjusted to 4.5 by introducing further zinc oxide. The suspension was filtered and the filtrate was spray dried with a lab spray drier (Büchi B-290 Advanced) to yield a white to yellowish powder. The content of the zinc sulfonate was 82 wt.-%, the content of zinc sulfite was 3.6 wt. %, as determined by iodometric titration.

EXAMPLE 2

Synthesis of a Magnesium-Salt of 2-Hydroxy-2-Sulfonatoacetic Acid

Under ice-cooling, 88.8 g of 50% glyoxylic acid (50% aqueous solution) was solved in 100 g of demineralized water and treated with 17.5 g of magnesium hydroxid in portions. 192.9 g of a 29% solution of magnesium bisulfite was added dropwise to the reactor and afterwards stirred for 1 h at room temperature. Then, the pH value was adjusted to 4.5 by introducing further magnesium hydroxide. The suspension was filtered and the filtrate was spray dried with a lab spray drier (Büchi B-290 Advanced) to yield a white powder. The content of the magnesium sulfonate was 98 wt.-%, the content of magnesium sulfite was 0.5 wt. %, as determined by iodometric titration.

EXAMPLE 3

Synthesis of a Mixed Magnesium-Zinc-Salt of 2-Hydroxy-2-Sulfonatoacetic Acid

Under ice-cooling, 44.4 g of glyoxylic acid (50% aqueous solution) was solved in 100 g of demineralized water and treated with 12.2 g of zinc oxide in portions. 96.4 g of a 29% solution of magnesium bisulfite was added dropwise to the reactor and afterwards stirred for 1 h at room temperature. Then, the pH value was adjusted to 4.5 by introducing further zinc oxide. The suspension was filtered and the filtrate was spray dried with a lab spray drier (Büchi B-290 Advanced) to yield a white powder. The content of the mixed magnesium-zinc sulfonate was 98 wt.-%, the content of mixed magnesium-zinc sulfite was 0.5 wt. %, as determined by iodometric titration. The weight ratio of zinc and magnesium was 1:1.05, as determined by complexometric titration.

EXAMPLE 4

Synthesis of a Mixed Magnesium-Aluminium-Salt of 2-Hydroxy-2-Sulfonatoacetic Acid Under ice-cooling, 44.4 g of glyoxylic acid (50% aqueous solution) was solved in 100 g of demineralized water and treated with 11.7 g of aluminium hydroxide in portions. 96.4 g of a 29% solution of magnesium bisulfite was added dropwise to the reactor and afterwards stirred for 1 h at room temperature. Then, the pH value was adjusted to 4.5 by introducing further aluminium hydroxide. The suspension was filtered and the filtrate was spray dried with a lab spray drier (Büchi B-290 Advanced) to yield a white powder. The content of the mixed magnesium-aluminum sulfonate was 85 wt.-%, the content of mixed magnesium-aluminum sulfite was 2.5 wt. %, as determined by iodometric titration. The weight ratio of magnesium and aluminum was 2.24:1, as determined by atomic absorption spectroscopy.

EXAMPLE 5

Synthesis of a Mixed Magnesium-Calcium-Salt of 2-Hydroxy-2-Sulfonatoacetic Acid Under ice-cooling, 44.4 g of glyoxylic acid (50% aqueous solution) was solved in 100 g of demineralized water and treated with 8.7 g of calcium hydroxide in portions. 96.4 g of a 29% solution of magnesium bisulfite was added dropwise to the reactor and afterwards stirred for 1 h at room temperature. Then, the pH value was adjusted to 4.5 by introducing magnesium hydroxide. The suspension was filtered and the filtrate was spray dried with a lab spray drier (Büchi B-290 Advanced) to yield a white powder. The content of the mixed magnesium-calcium sulfonate was 82 wt.-%, the content of mixed calcium-magnesium sulfite was 4 wt. %, as determined by iodometric titration. The weight ratio of magnesium and calcium was 2.94:1, as determined by complexometric titration.

EXAMPLE 6

Color Stabilization of Superabsorbent Polymers 100 g of commercially available SAP powder (ST-001, Zhejiang Satelliate Petrochemical Ltd.) were treated with 3 g of a 1% solution of the sulfonic acid salts of Examples 1-3 (invention), and of 2-hydroxy-2-sulfonatoacetic acid disodium salt (comparative). An untreated aliquot was used as a control.

The samples were stored at 60° C. and 90% relative humidity for 25 days.

The sample color was assessed by the Hunter b-value. This test measures the perceived color of a polymer related to its spectral characteristics. Spectral characteristics are specified by reflectance as a function of wavelength. In this system, "b" is a measure of yellowness (positive b-values) or blueness (negative b-values). The measurement was performed on the polymer powder using a X-rite Color Master SP60 Spectrophotometer (X-rite).

| Color stabilization | b-value (day 0) | Increase in b-value (after 26 days) in % |
|---|---|---|
| Example 1 | | +18.3 |
| Example 2 | 3.01 | +15.3 |
| Example 3 | | +11.7 |
| disodium salt of 2-hydroxy-2-sulfonatoacetic acid (comparative) | | +16.7 |
| Control sample (without additive) | | +25.7 |

EXAMPLE 7

Assessment of Odor Characteristics

Further, the odor characteristics of the samples of examples 1-5 were assessed. The samples to be tested were provided to a panel of two odor specialists who independently rank the odor of the samples on a scale of 1 (least) to 5 (most) for malodor and intensity. Samples yielding an odor ranking of 1 possess an odor which would hardly be noticed by the general public.

The results are summarized in the following table:

| Odor ranking | 1 | 2 | 3 | 4 | 5 |
|---|---|---|---|---|---|
| Example 1 | x | | | | |
| Example 2 | | x | | | |
| Example 3 | x | | | | |
| Example 4 | | | | x | |
| Example 5 | | | | x | |
| disodium salt of 2-hydroxy-2-sulfonatoacetic acid (comparative) | | | | | x |

EXAMPLE 8

Aqueous Solubility

Aqueous solubility was determined by adding aliquots of the sulfonic acid salts of Examples 1-5 and of disodium salt of 2-hydroxy-2-sulfonatoacetic acid to water according to OECD 105.

| Solubility ranking | Solubility in water at 23° C. |
|---|---|
| Example 1 | 39% |
| Example 2 | 20% |
| Example 3 | 39% |
| Example 4 | 42% |
| Example 5 | 23% |
| disodium salt of 2-hydroxy- | 7% |

| Solubility ranking | Solubility in water at 23° C. |
|---|---|
| 2-sulfonatoacetic acid (comparative) | 5 |

The invention claimed is:

1. A sulfonic acid salt composition comprising compounds of formula (I)

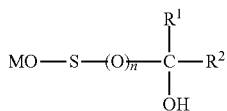

wherein
n is 1 or 2,
$R^1$ is H or $C_1$-$C_6$ alkyl,
$R^2$ is COOM, $SO_3M$ or $CH(OH)SO_2$—OM,
each M is an equivalent of a multivalent metal, and
the molar ratio of a compound wherein n is 1 to a compound wherein n is 2 is below 0.1.

2. The sulfonic acid salt composition of claim 1, wherein M is selected from groups 2, 4, 12 and 13 of the Periodic Table of Elements.

3. The sulfonic acid salt composition of claim 2, wherein M is selected from magnesium, calcium, aluminum, zinc and combinations thereof.

4. The sulfonic acid salt composition of claim 3, wherein M comprises a combination of first metal $M^1$ and a second metal $M^2$, wherein $M^1$ is selected from zinc, calcium and aluminum, and $M^2$ is magnesium.

5. The sulfonic acid salt composition of claim 4, wherein M comprises, on an equivalent basis, 10 to 70 mole % of $M^1$ and 30 to 90 mole % of $M^2$.

6. The sulfonic acid salt composition of claim 3, wherein $M^1$ is zinc.

7. The sulfonic acid salt composition of claim 1, wherein $R^1$ is H.

8. The sulfonic acid salt composition of claim 1, wherein $R^2$ is COOM.

9. A process for preparing the sulfonic acid salt composition according to claim 1, comprising reacting a glyoxylic acid salt of a first metal $M^1$ with a bisulfite salt of a second metal $M^2$, wherein $M^1$ and $M^2$ each are multivalent metals which can be identical or different.

10. The process of claim 9, wherein $M^1$ and $M^2$ are independently selected from magnesium, calcium, aluminum, and zinc.

11. The process of claim 9, wherein $M^1$ is selected from zinc, calcium and aluminum, and $M^2$ is magnesium.

12. The process of claim 9, wherein the pH of the reaction medium is adjusted to 4 to 5 by addition of an oxide or hydroxide of $M^1$.

13. The process of claim 9, wherein the glyoxylic acid salt of the first metal $M^1$ is prepared by reacting glyoxylic acid with an oxide or hydroxide of $M^1$ in an aqueous medium and the glyoxylic acid salt of the first metal $M^1$ is reacted in a one-pot reaction with the bisulfite salt of the second metal $M^2$ without prior isolation or purification.

14. A method comprising using the sulfonic acid salt composition of claim 1 for color stabilization of non-living organic matter.

15. The method of claim 14, wherein the non-living organic matter is selected from lacquers, paints, powder-coatings, and polymers.

16. The method of claim 15, wherein the polymer is selected from water-absorbent polymers.

17. The method of claim 16, wherein the water-absorbent polymer comprises a polyacrylic acid and/or salt thereof.

18. The sulfonic acid salt composition of claim 4, wherein M comprises, on an equivalent basis, 10 to 45 mole % of $M^1$ and 55 to 90 mole % of $M^2$.

19. The sulfonic acid salt composition of claim 4, wherein $M^1$ is zinc.

20. The sulfonic acid salt composition of claim 5, wherein $M^1$ is zinc.

* * * * *